United States Patent

Lindberg et al.

[11] 4,073,941
[45] Feb. 14, 1978

[54] ARALKYL AMIDES HAVING ANTIDEPRESSIVE ACTIVITY

[75] Inventors: Ulf Henrik Anders Lindberg; Svante Bertil Ross, both of Sodertalje; Seth Olov Thorberg, Jarna; Sven Ove Ögren, Sodertalje, all of Sweden

[73] Assignee: Astra Lakemedel Aktiebolag, Sodertalje, Sweden

[21] Appl. No.: 718,570

[22] Filed: Aug. 30, 1976

[30] Foreign Application Priority Data

Sept. 4, 1975 Sweden .............................. 75098137

[51] Int. Cl.² ................. A61K 31/165; C07C 103/10; C07C 103/32
[52] U.S. Cl. ................. 424/324; 260/562 N
[58] Field of Search ................. 260/562 N; 424/324

[56] References Cited

U.S. PATENT DOCUMENTS 3,692,784  9/1972  Lindberg ......................... 260/247.2
3,835,153  9/1974  Lindberg ......................... 260/326.43

FOREIGN PATENT DOCUMENTS 7,628M  1/1970  France.

OTHER PUBLICATIONS

Chem. Abst., 76 - 152718x (1972).
Chem. Abst., 83 - 10920c (1975).

Primary Examiner—Stanley J. Friedman
Attorney, Agent, or Firm—Brumbaugh, Graves, Donohue & Raymond

[57] ABSTRACT

A compound of the formula

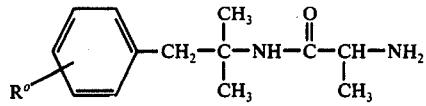

and pharmaceutically acceptable acid addition salts thereof, in which formula the group $R^o$ is selected from hydrogen, chlorine, bromine, methyl, trifluoromethyl and methoxy.

Pharmaceutical compositions containing these compounds are useful for treatment of depressive disorders.

15 Claims, No Drawings

ARALKYL AMIDES HAVING ANTIDEPRESSIVE ACTIVITY

This invention relates to new aralkyl amides of amino-acids, and processes for their preparation. This invention also relates to methods for the pharmacological use of these compounds and to pharmaceutical preparations containing such compounds.

An object of this invention is to provide compounds having effect on the central nervous system, especially antidepressive activity, and having a reduced frequency of side effects and increased effectiveness compared to drugs presently used in this area.

A further object of this invention is to provide pharmaceutical preparations containing as active ingredient a compound according to this invention.

Still an object of this invention is to provide methods for the treatment of depressive disorders.

The presently most used compound for controlling depressions is imipramine (Tofranil ®)

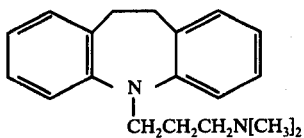
$CH_2CH_2CH_2N[CH_3]_2$

This compound is both mood elevating and psychomotor activating, but it possesses several disadvantages. It is anticholinergic and causes anticholinergic symptoms such as dryness of the mouth, tremor, tachycardia and sweating. In higher doses it can provoke serious heart arrhythmias and in normal doses it can cause toxic interactions in persons with heart failures. Furthermore, another drawback with treatment with imipramine is the late onset of the antidepressive effect, which effect is observable first after about 3 weeks of treatment.

It has been shown that imipramine has an effect on the action of the transmitter substances in the central nervous system. More specifically, imipramine inhibits the re-uptake mechanism of noradrenaline (NA) and 5-hydroxytryptamine (5-HT). The mood elevation part of the antidepressive action is assumed to be mainly related to the inhibition of 5-HT uptake.

According to the present invention we have found that certain new compounds, which can be described as aralkyl amides of amino acids, can be used for inhibiting selectively the central neuronal uptake of 5-hydroxytryptamine. Further the heart toxicities for these new compounds are considerably weaker than those of imipramine.

The new compounds according to the invention can be described by the general formula

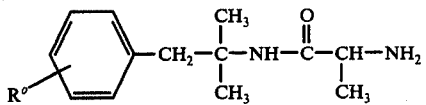

in which formula the group $R^o$ is selected from the group consisting of hydrogen, chlorine, bromine, methyl, trifluoromethyl, and methoxy, including pharmaceutically acceptable acid-addition salts.

Since these new compounds contain an asymmetric carbon atom, they exist in the form of optically active forms, and can be resolved into their optical antipodes by well known methods such as by using optically active acids such as tartaric acid, camphor-10-sulphonic acid, dibenzoyl tartaric acid, and the like.

A subgroup of compounds within the invention is obtained when, in the formula I above, the group $R^o$ is selected from the group consisting of hydrogen, chlorine, bromine, methyl and methoxy.

A preferred subgroup of compounds within the invention is obtained when, in the formula I above, the group $R^o$ is placed in para-position. A further preferred subgroup of compounds is obtained when the group $R^o$ is selected from chlorine, bromine and methyl. A particularly preferred subgroup is obtained when the group $R^o$ is placed in para-position, and is selected from chlorine, bromine and methyl.

The following compounds can be mentioned as examples of compounds included in the invention:

2-Amino-$N^1$-[3-(4-chlorophenyl)-2-methyl-2-propyl] propanoic acid amide

2-Amino-$N^1$-[3-(4-bromophenyl)-2-methyl-2-methyl-2-propyl] propanoic acid amide 2-Amino-$N^1$-[3-(4-methylphenyl)-2-methyl-2-propyl] propanoic acid amide 2-Amino-$N^1$-[3-(4-trifluoromethylphenyl)-2-methyl-2-propyl] propanoic acid amide 2-Amino-$N^1$-[3-(3-methylphenyl)-2-methyl-2-propyl] propanoic acid amide 2-Amino-$N^1$-[3-phenyl-2-methyl-2-propyl] propanoic acid amide The compounds of the present invention can be prepared by a. reacting a compound of the formula

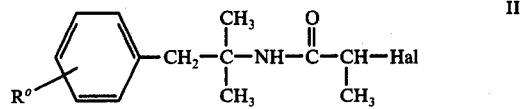

in which formula Hal is Cl or Br, with ammonia to the formation of a compound of the formula I; or b. reducing a carbamate of the formula

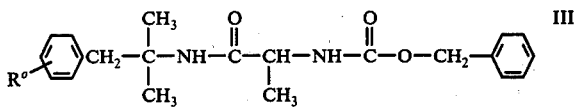

by catalytic hydrogenation to the formation of a compound of the formula I in which formulas $R^o$ has the meaning given above.

The reactions according to (a) or (b) are preferably conducted in an inert organic solvent capable of dissolving the reactants. Any suitable pressure and reaction temperature can be used. Preferably, the reactions are carried out under atmospheric or superatmospheric pressure, at a temperature of between $-10°$ to $+100°$ C, preferably between $0°-30°$ C.

Intermediates of the formulas II and III are novel compounds, and constitutes a further aspect of the invention.

Intermediates of the formulas II can e.g. be prepared by reacting a compound of the formula

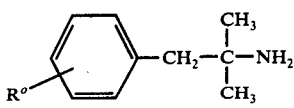

with a compound of the formula

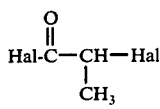

wherein R° and Hal have the meanings given above.

The intermediate of the formula III can be prepared by reacting a compound of the formula IV with a compound of the formula

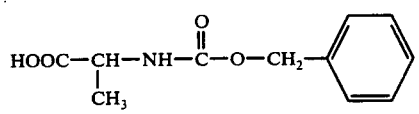

in the presence of dicyclohexyl carbodiimide.

The new compounds of this invention may be used therapeutically as the racemic mixtures of (+)- and (−)-forms, which in the usual case are obtained at the synthesis. They may also be resolved by methods known per se into the corresponding optically active modifications which, likewise, may be used in therapy. If desired, the optically active modification can be prepared by way of direct synthesis, e.g. via an optically active compound of the formula VI as described above.

b. Pharmaceutical preparations

In clinical practice the compounds of the present invention will normally be administered orally, rectally or by injection, in the form of pharmaceutical preparations comprising the active ingredient either as a free base or as a pharmaceutically acceptable non-toxic, acid addition salt, e.g. the hydrochloride, hydrobromide, lactate, acetate, phosphate, sulphate, sulphamate, citrate, tartrate, oxalate and the like in association with a pharmaceutically acceptable carrier. Accordingly, terms relating to the novel compounds of this invention whether generically or specifically are intended to include both the free amine base and the acid addition salts of the free base, unless the context in which such terms are used, e.g. in the specific examples would be inconsistent with the broad concept. The carrier may be a solid, semisolid or liquid diluent or capsule. These pharmaceutical preparations, which contain between 0.1 and 95% by weight of the active substance, constitute a further aspect of this invention. Usually the active substance will constitute between 0.5 and 20% by weight for preparations intended for injection and between 2 and 50% by weight for preparations suitable for oral administration.

To produce pharmaceutical preparations containing a compound of the invention in the form of dosage units for oral application the selected compound may be mixed with a solid pulverulent carrier, e.g. lactose, saccharose, sorbitol, mannitol, starches such as potato starch, corn starch or amylopectin, cellulose derivatives, a binder such as gelatine or polyvinylpyrrolidone, and a lubricant such as magnesium stearate, calcium stearate, polyethylene glycol waxes, and the like, and then compressed to form tablets. If coated tablets are required, the cores, prepared as described above, may be coated with a concentrated sugar solution which may contain, e.g. gum arabic, gelatine, talcum, titanium dioxide, and the like. Alternatively, the tablet can be coated with a lacquer dissolved in a readily volatile organic solvent or mixture of organic solvents. Dyestuffs may be added to these coatings in order to readily distinguish between tablets containing different active substances or different amounts of the active compounds.

For the preparation of soft gelatine capsules (pearl-shaped closed capsules) consisting of gelatine and for example, glycerol or similar closed capsules, the active substance may be admixed with a vegetable oil. Hard gelatine capsules may contain granulates of the active substance in combination with solid, pulverulent carriers such as lactose, saccharose, sorbitol, mannitol, starches (e.g. potato starch, corn starch or amylopectin), cellulose derivatives or gelatine.

Dosage units for rectal application can be prepared in the form of suppositories comprising the active substance in admixture with a neutral fatty base, or gelatine rectal capsules comprising the active substance in admixture with vegetable oil or paraffin oil.

Liquid preparations for oral application may be in the form of syrups or suspensions, for example, solutions containing from about 0.2% to about 20% by weight of the active substance herein described, the balance being sugar and a mixture of ethanol, water, glycerol, and propyleneglycol. Optionally such liquid preparations may contain colouring agents, flavouring agents, saccharine and carboxymethylcellulose as a thickening agent.

Solutions for parenteral applications by injection can be prepared in the form of an aqueous solution of a water-soluble pharmaceutically acceptable salt of the active substance preferably in a concentration of from about 0.5% to about 10% by weight. These solutions may also contain stabilizing agents and/or buffering agents and may conveniently be provided in various dosage unit ampoules.

Suitable daily doses of the compounds of the invention at therapeutical treatment is 100 to 500 mg at peroral administration and 20 to 100 mg at parenteral administration.

The preferred compound of the invention has the formula (GEA 609)

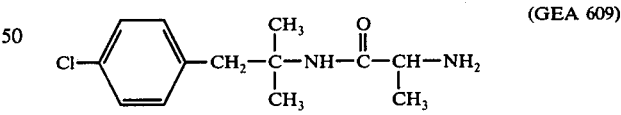

Preferably this compound is prepared and used in the form of its hydrochloride salt.

The preparation of compounds according to the invention is illustrated in the following example.

Preparation of
2-amino-N¹-[3-(4-chlorophenyl)-2-methyl-2-propyl] propanoic acid amide Method A 3-(4-Chlorophenyl)-2-methyl-2-propylamin (IV) was prepared according to a known method [Farmaco (Pavia) Ed. Sci. 15 337 (1960), Ferrari, G.]

The above amine (IV) (30.0 g; 0.163 mole) was dissolved in toluene (140 ml) and 10% sodium hydroxide solution (200 ml). The mixture was cooled to −5° C and 2-bromopropanoic acid bromide (62.2 g; 0.288 mole) was added dropwise during 20 minutes while vigorously stirring the two phase system. Stirring was continued at room temperature for 2 hours. After filtration and washing the precipitate with water and toluene, the white product of 2-bromo-N-[3-(4-chlorophenyl)-2-methyl-2-propyl] propanoic acid amide (II) was dried in vacuo. Yield: 48.4 g (93%), M.p. 122°–123° C The bromoamide (II) (10.0 g; 0.031 mole) was dissolved in absolute ethanol (250 ml). The solution was cooled on ice and saturated with ammonia gas (5 hours). The total time for amination was 6 days at room temperature and the saturation with $NH_3(g)$ was repeated once a day. The solvent was removed under vacuum. The residual oil was dissolved in ether (100 ml) and the solution was extracted with 0.5 N hydrochloric acid (100 ml). The acidic phase was made alkaline with 1 N sodium hydroxide solution (pH = 10) and was extracted twice with ether. After drying and evaporation a colourless oil was obtained, from which the hydrochloride was prepared. After recrystallization from chloroform and ethylacetate the yield of 2-amino-$N^1$-[3-(4-chlorophenyl)-2-methyl-2-propyl] propanoic acid amide (I) hydrochloride was 5.2 g (57%), melting at 180°–181° C.

Method B

N-Carbobenzoxyalanine (4.5 g; 0.020 mole) was dissolved in methylene chloride (45 ml) and cooled on ice. Dicyclohexyl carbodiimide (DCC) (4.1 g; 0.020 mole) was added in portions under stirring which was continued for 15 minutes. A thick, white precipitate was obtained. To this mixture was added during 10 minutes a solution of 3-(4-chlorophenyl)-2-methyl-2-propylamin (IV) (see Method A) (3.7 g; 0.020 mole) in methylene chloride (10 ml). Stirring was continued at room temperature for 1.5 hours. The mixture was filtered and the filtrate was washed with water, 3 N hydrochloric acid, saturated sodium hydrogen carbonate and saturated sodium chloride solution. Drying and evaporation of the organic phase afforded a viscous, colourless oil (7.2 g; 93%).

The carbobenzoxy protected product (III) above (7.0 g; 0.018 mole) was dissolved in a 0.2 N solution of hydrogen chloride in absolute ethanol (150 ml) and the solution was cooled on ice. Nitrogen gas was lead through the solution and palladium on charcoal (5%, 2.0 g) was added. Cooling and stirring under $N_2$-atmosphere was continued for 10 minutes. Hydrogen gas was then lead into the mixture during 3 hours. After the reaction the excess hydrogen was removed by a stream of nitrogen (15 min). The catalyst was filtered off and the filtrate was evaporated in vacuo affording a white crystalline product which was recrystallized from ethyl acetate. The melting point was 180°–181° C and the yield was 4.3 g (83%) of the desired 2-amino-$N^1$-[3-(4-chlorophenyl)-2-methyl-2-propyl] propanoic acid amide (I) hydrochloride.

Pharmacological methods

A. Biochemical tests

1. Inhibition of the uptake of carbon-14 5-HT and tritiated noradrenaline in vitro and in vivo The method is described by Ross, Renyi and Ogren in European Journal of Pharmacology 17 (1972), 107–112. Tricyclic antidepressant drugs of type imipramine added in vitro or given in vivo to mice decrease the uptake of $^{14}C$-5-HT and $^3H$-NA in vitro. In the in vitro experiments different concentrations of the test compound were added to the incubation medium. In the in vivo experiments different doses of the test drug were administered intraperitoneally half an hour before the animals were killed. The incubation performance was the same in the two types of experiments, i.e. the midbrain was taken out and sliced and incubated in a mixture consisting of, per 100 mg of brain slices, 0.2 n-mole of $^{14}C$-5-HT, 0.2 n-mole of $^3H$-NA and 11 μmole of glucose in 2 ml of Krebs-Henseleit buffer, pH 7.4. The incubation time was 5 minutes. The radioactive amines taken up in the slices were dissolved in Soluene-350 ® (Packard) and the amounts were determined with the double labelling technique by liquid scintillation. The concentration or dose producing 50 percent decrease of the active uptake ($ED_{50}$) was determined graphically from dose-response curves. Active uptake is defined as that part of the radioactive uptake which is inhibited by a high concentration of cocaine. All doses were given at least to four animals.

B. Pharmacological tests 1. 5-HTP response potentiation test

Inhibition of the uptake of 5-HT potentiates the effects of administered 5-hydroxytryptophan (5-HTP) probably by increasing the amount of 5-HT at the receptor. Three mice are given the test drugs 1 hour (or 4, 24 hours) before dl-5-HTP 90 mg/kg i.v. 5-HTP alone gives only a weak behavioural syndrome but in pretreated mice there is seen a characteristic behavioural syndrome, which comes within 5 minutes: tremor, lordosis, abduction of the hindlegs, head-twiches. The strength of the syndrome is scored from 0 to +3. Each group consists of 3 animals and at least 4 groups were tested at 25 mg/kg i.p. Control groups receiving imipramine (Tofranil ®) are used as reference, since imipramine constantly potentiated dl-5-HTP. The least dose of the test compound producing maximal score (+3) in all animals is estimated from a logarithmic dose-response curve, and is denoted "effective dose" in the following Table.

The results from the above described tests are summarized in the following Table. The code number GEA 609 represent the compound 2-amino-$N^1$-[3-(4-chlorophenyl)-2-methyl-2-propyl] propanoic acid amide hydrochloride, i.e. a compound according to the invention.

Table

| Compound | Inhibition (50 %) of uptake | | | | Potentiation of 5-HTP[3] effective dose (mg/kg i.p.) |
|---|---|---|---|---|---|
| | in vitro 5-HT[1] (μg/ml) | NA[2] | in vivo 5-HT[1] (mg/kg i.p.) | NA[2] | |
| GEA 609 | 0.7 | >10 | 20 | >40 | 0.5 |
| Imipramine | 0.1 | 0.06 | 24 | 6 | 15 |

[1] 5-HT = 5-hydroxytryptamine, $1 \times 10^{-7}M$
[2] NA = 1-noradrenaline, $1 \times 10^{-7}M$
[3] 5-HTP = 5-Hydroxytryptophan
i.p. = intraperitoneal administration Evaluation of the results obtained in the pharmacological tests The compounds of the invention block the uptake of 5-hydroxytryptamine in brain slices in vitro and in vivo but do not inhibit the uptake of noradrenaline. In vivo they are more potent than imipramine as inhibitors of the 5-hydroxytryptamine. They potentiate the responses of 5-hydroxytryptophan at considerably lower doses than imipramine.

These results indicate that the new compounds are much more selective than imipramine in inhibiting the uptake of 5-hydroxytryptamine.

Pharmaceutical compositions

The following examples illustrates the preparation of pharmaceutical compositions according to the invention. For the preparation of tablets the following compositions were made

| a) | 2-Amino-N¹-[3-(4-chlorophenyl)-2-methyl-2-propyl]propanoic acid amide hydrochloride (GEA 609) | 50 g |
| | Lactose | 85 g |
| | Potatoe starch | 40 g |
| | Polyvinylpyrrolidone | 5 g |
| | Cellulose Avicel | 18 g |
| | Magnesium stearate | 2 g |
| b) | 2-Amino-N¹-[3-(4-chlorophenyl)-2-methyl-2-propyl]propanoic acid amide hydrochloride (GEA 609) | 100 g |
| | Lactose | 90 g |
| | Potatoe starch | 50 g |
| | Polyvinylpyrrolidone | 5 g |
| | Cellulose Avicel | 23 g |
| | Magnesium stearate | 2 g |

From the above compositions 1000 tablets were made, containing 50 mg and 100 mg of active substance, respectively. If desired, the obtained tablets can be film coated with e.g. methyl cellulose in an organic solvent.

We claim:

1. A compound of the general formula

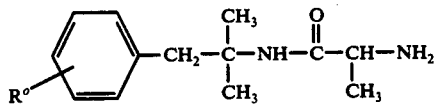

(I)

or a pharmaceutically acceptable acid addition salt thereof, in which formula the group R⁰ is selected from the group consisting of hydrogen, chlorine, bromine, methyl, trifluoromethyl and methoxy.

2. A compound according to claim 1, in which formula the group R⁰ is selected from the group consisting of hydrogen, chlorine, bromine, methyl and methoxy.

3. A compound according to claim 1, in which formula the group R⁰ is selected from the group consisting of chlorine, bromine and methyl.

4. A compound according to claim 1, in which formula the group R⁰ is placed in para-position and is selected from the group consisting of chlorine, bromine and methyl.

5. A compound according to claim 1 of the formula

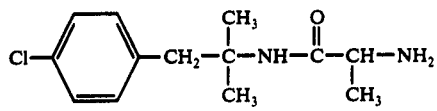

or a pharmaceutically acceptable acid addition salt thereof.

6. A pharmaceutical composition comprising as active ingredient between 0.1 and 95% by weight of the composition of a compound as claimed in claim 1, together with a pharmaceutically acceptable carrier, for use in the treatment of depressive disorders related to neuronal uptake of 5-hydroxytryptamine.

7. A pharmaceutical composition comprising as active ingredient between 0.1 and 95% by weight of the composition of a compound as claimed in claim 2, together with a pharmaceutically acceptable carrier, for use in the treatment of depressive disorders related to neuronal uptake of 5-hydroxytryptamine.

8. A pharmaceutical composition comprising as active ingredient between 0.1 and 95% by weight of the composition of a compound as claimed in claim 3, together with a pharmaceutically acceptable carrier, for use in the treatment of depressive disorders related to neuronal uptake of 5-hydroxytryptamine.

9. A pharmaceutical composition comprising as active ingredient between 0.1 and 95% by weight of the composition of a compound as claimed in claim 4, together with a pharmaceutically acceptable carrier, for use in the treatment of depressive disorders related to neuronal uptake of 5-hydroxytryptamine.

10. A pharmaceutical composition comprising as active ingredient between 0.1 and 95% by weight of the composition of a compound as claimed in claim 5, together with a pharmaceutically acceptable carrier, for use in the treatment of depressive disorders related to neuronal uptake of 5-hydroxytryptamine.

11. A method for the treatment of depressive disorders related to neuronal uptake of 5-hydroxytryptamine, the method comprising administration to a host in need of such treatment of a therapeutically effective amount of a compound as claimed in claim 1.

12. A method for the treatment of depressive disorders related to neuronal uptake of 5-hydroxytryptamine, the method comprising administration to a host in need of such treatment of a therapeutically effective amount of a compound as claimed in claim 2.

13. A method for the treatment of depressive disorders related to neuronal uptake of 5-hydroxytryptamine, the method comprising administration to a host in need of such treatment of a therapeutically effective amount of a compound as claimed in claim 3.

14. A method for the treatment of depressive disorders related to neuronal uptake of 5-hydroxytryptamine, the method comprising administration to a host in need of such treatment of a therapeutically effective amount of a compound as claimed in claim 4.

15. A method for the treatment of depressive disorders related to neuronal uptake of 5-hydroxytryptamine, the method comprising administration to a host in need of such treatment of a therapeutically effective amount of a compound as claimed in claim 5.

* * * * *